United States Patent [19]

McLeod

[11] 4,227,531
[45] Oct. 14, 1980

[54] PANTY LINER CONSTRUCTION

[76] Inventor: Syble A. McLeod, Box 64, Iron City, Ga. 31759

[21] Appl. No.: 914,593

[22] Filed: Jun. 12, 1978

[51] Int. Cl.³ .................. A61F 13/16; A41B 9/04
[52] U.S. Cl. ........................................ 128/288; 2/406
[58] Field of Search .............. 128/288, 289; 2/406, 2/407

[56] References Cited

U.S. PATENT DOCUMENTS

| 1,904,228 | 4/1933 | Hennessy | 128/288 |
| 2,165,561 | 7/1939 | Marcus | 128/288 |
| 2,493,357 | 1/1950 | Miller | 2/406 |
| 2,555,434 | 6/1951 | Anderson | 128/288 |
| 2,736,029 | 2/1956 | Diogene | 2/406 |

FOREIGN PATENT DOCUMENTS

| 2285088 | 5/1976 | France | 2/406 |
| 2943 | 7/1891 | Sweden | 2/407 |
| 256492 | 3/1949 | Switzerland | 2/406 |

*Primary Examiner*—Robert W. Michell
*Assistant Examiner*—C. W. Shedd
*Attorney, Agent, or Firm*—B. J. Powell

[57] ABSTRACT

A panty liner construction including an interior liquid absorbent layer, an intermediate liquid impermeable layer which may be permanently incorporated in or removably connected to a fabric panty where the liner defines leg openings therethrough connected to the panty to accommodate different size persons within a prescribed range.

5 Claims, 9 Drawing Figures

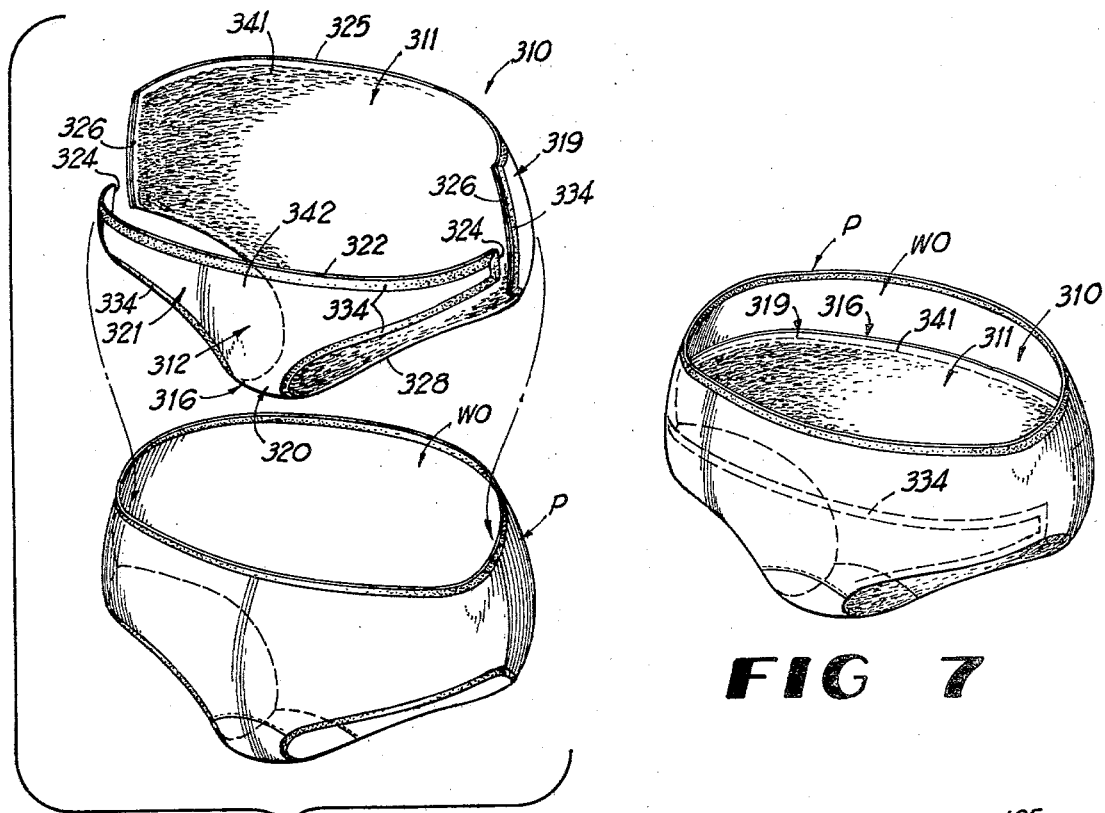
FIG 6
FIG 7
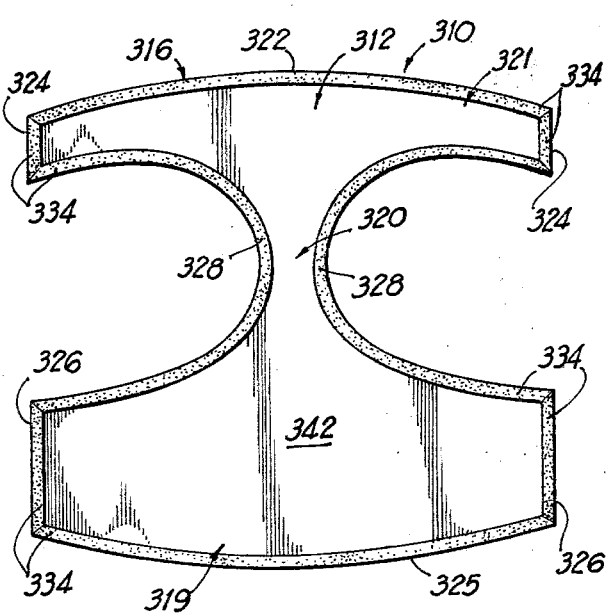
FIG 8
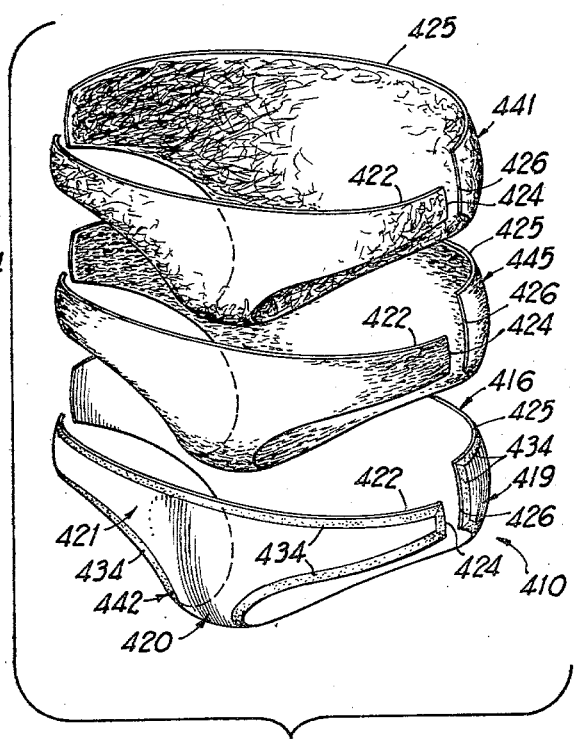
FIG 9

PANTY LINER CONSTRUCTION

BACKGROUND OF THE INVENTION

A wide variety of panty constructions are available on the market today. Such panty constructions usually consist of fabric layer with a waist opening and leg openings. One of the problems with these prior art panty constructions is that any liquid exposed to the interior of the panty is also absorbed by the exteriorly exposed fabric layer of the panty which is undesirable. Some of these prior art panty constructions have had a soft liquid absorbent interior layer in the crotch section which sometimes delayed, but did not prevent, the liquid from being absorbed by the exterior fabric layer of the panty construction. Other attempts to alleviate this problem usually included a separate unit with a relatively thick absorbent layer that was worn inside the panty construction or in lieu of the panty construction. Such attempts at alleviating this problem have not been satisfactory because they were bulky and thus unsightly when worn plus such attempts frequently leaked so that the liquids were eventually absorbed by the exterior fabric layer.

SUMMARY OF THE INVENTION

These and other problems and disadvantages associated with the prior art are overcome by the invention disclosed herein by a panty construction in which the liquids to which the interior of the panty construction is exposed will not be absorbed by the fabric layer of the panty construction. Further, the construction is sufficiently thin to be worn without the problems of bulkiness and unsightliness. Moreover, the invention provides an adjustablility which permits the panty construction to adjust to different body configurations normally found in a particular size range.

One embodiment of the panty construction includes an interior absorbent layer, an exterior fabric layer, and a liquid impermeable layer sandwiched between the interior and exterior layers so that the interior layer will absorb any liquids to which the interior of the panty construction is exposed while the intermediate layer prevents the exterior layer from absorbing such liquid. The intermediate layer may have a one-piece construction to prevent leakage therethrough while the interior and exterior layers may have multiple-piece constructions to facilitate assembly. The layers may be appropriately sewn together so that the panty construction is unitary. An elastic adjustment member is connected to the liquid impermeable layer to insure that the liquid impermeable layer smoothly conforms to the body configuration of the wearer even though such body configurations may vary from wearer to wearer. The panty construction may have ventilated panels incorporated therein for comfort, especially in the elastic adjustment member.

Another embodiment of the invention is designed to fit in a conventional panty to convert the panty construction into a panty construction with the advantage of the above embodiment. This embodiment has an interior absorbent layer and an exterior liquid impermeable layer which fit within the panty. The exterior layer is provided with adhesive strips to positively attach the invention to the panty.

These and other features and advantages of the invention will become more clearly understood upon consideration of the following specification and accompanying drawings herein like characters of reference designate corresponding parts throughout the several views and in which:

BRIEF DESCRIPTION OF THE DRAWINGS

FIG. 6 is an exploded perspective view of a fourth embodiment of my invention;

FIG. 7 is a perspective view of that embodiment of the invention shown in FIG. 6 assembled;

FIG. 8 is a folded out view of the invention seen in FIGS. 6 and 7; and

FIG. 9 is an exploded perspective view of a fifth embodiment of my invention.

These figures and the following detailed description disclose specific embodiments of the invention; however, it is to be understood that the inventive concept is not limited thereto since it may be embodied in other forms.

DETAILED DESCRIPTION OF ILLUSTRATIVE EMBODIMENTS

Figure 1:
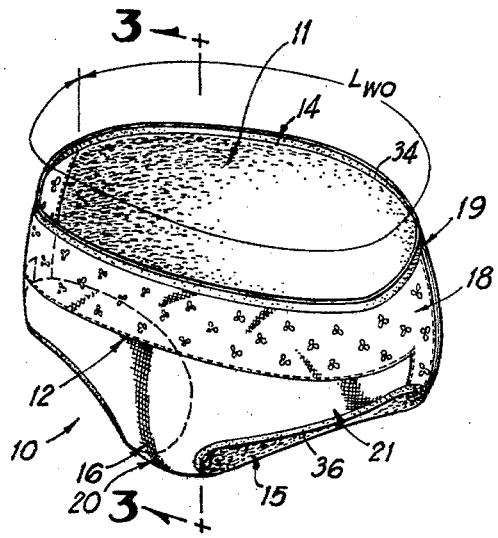
FIG. 1 is a perspective view of a panty construction embodying my invention.
Figure 2:
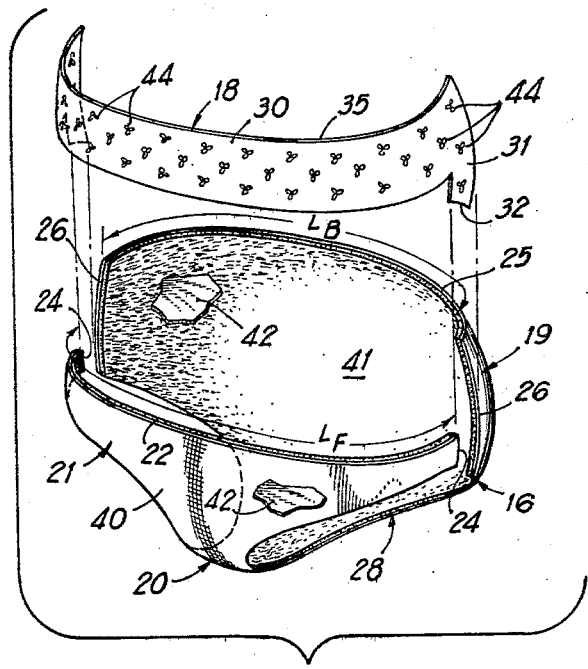
FIG. 2 is an exploded perspective view of the panty construction of FIG. 1.
Figure 3:
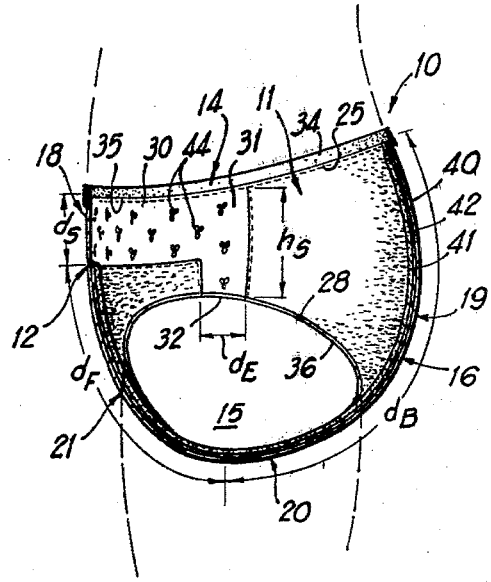
FIG. 3 is a cross-sectional view taken generally along line 3—3 in FIG. 1.

Referring to FIGS. 1–3, it will be seen that the first embodiment of the invention is incorporated in a panty 10 having an interior 11 and an exterior 12 with a waist opening 14 at its top and pair of leg openings 15 at its lower section so that the panty 10 can be worn similarly to conventional panties. The panty 10 is made up of a non-stretchable panel assembly 16 and a stretch panel 18 so that the panty can conform to different body configurations in the same size range.

The non-stretchable panel assembly 16 has a back section 19, a crotch section 20 and a front section 21. The back section 19 extends from the waist opening 14 down to the crotch section 20, but the front section 21 is shorter than the back section and extends up from the crotch section to a point below the waist opening. As best seen in FIG. 2, the front section 21 of the non-stretchable panel assembly 16 has an upper edge 22 spaced below the waist opening 14 and parallel to the edge of the waist opening. The front section 21 also has a pair of opposed size edges 24 which extend from opposite ends of the upper edge 22 to the leg opening 15 and are oriented generally perpendicular to the edge of the waist opening 14. Similarly, the back section 19 of the non-stretchable panel assembly 16 also has an upper edge 25 located along the edge of waist opening 14, and a pair of opposed size edges 26 which extend from opposite ends of the upper edge 25 down to the leg opening 15 and are oriented perpendicular to the edge of the waist opening 14. It will be noted that the waist opening 14 has an edge length $L_{WO}$ seen in FIG. 1 which is larger than the sumer of the length $L_B$ (FIG. 2) of the upper edge 25 of the back section 19 plus the length $L_F$ (FIG. 2) of the upper edge 22 of the front section 21 so that when the panel assembly 16 is formed into the panty shape as seen in FIG. 2, the side edges 24 of the front section 21 will be spaced from the side edges 26 of the back section 19 the distance $d_E$ (FIG. 3) as will become more apparent. It will also be noted that the distance $d_F$ from the middle of the crotch section 20 to the upper edge 22 of the front section 21 as seen in FIG. 3 is less than the distance $d_b$ from the middle of the crotch section 20 to the upper edge 25 of the back section 19 so that the upper edge 22 of the front section 21 is located below the edge of the waist opening 14 the distance $d_S$ seen in FIG. 3. The leg cutouts 28 in the non-stretchable panel assembly 16 form most of the leg openings 15 when the panel 16 is formed into the panty shape as seen in FIG. 2 with a portion of the top of the leg openings 15 being completed by the stretchable panel 18 as seen in the FIGS. 1–3.

The stretchable panel 18 connects the front section 21 to the back section 19 of the panel assembly 16 to complete the panty shape. The panel 18 has a central section 30 which is attached to the upper edge 22 of the front section 21 of panel assembly 16 and a pair of side sections 31 at opposite ends of the central section 30 which extend from the top of the leg openings 15 to the edge of the waist opening 14. The side sections 31 are attached to the adjacent front side edges 24 and back side edges 26 as seen in FIGS. 1 and 3. The central section 30 has a height about equal to the distance $d_S$ and a length about equal to length $L_F$ of the front section 21 of panel assembly while the side sections 31 each have a width about equal to the distance $d_E$ and a height $h_S$ (FIG. 3) sufficient to extend from the top of the leg opening 15 to waist opening 14. The lower edges 32 of the side sections 31 are shaped to complete the formation of the leg openings 15 as best seen in FIG. 3.

The waist opening 14 has an elasticized binding 34 sewed along the upper edge 26 of the back section 19 of the panel assembly 16 and the upper edge 35 of the stretchable panel 18. Similarly, an elasticized binding 36 is sewed to the panel assembly 16 along each leg cutout 28 and the connecting lower edge 32 of the side sections 31 of the stretchable panel 18 to bind each leg opening 15.

The non-stretchable panel assembly 16 has three layers, an exterior fabric layer 40, an interior moisture absorbent layer 41, and an intermediate moisture impermeable layer 42 with the three layers in juxtaposition with each other as best seen in FIG. 2. All of these layers have the same size and configuration with a front section, a crotch section and a back section along with the leg cutouts so that when they are attached together, the panel assembly 16 is formed. The exterior fabric layer 40 is a thin woven fabric material similar to that normally used in panty constructions such as woven nylon or rayon acetate. The interior layer 41 is made of a material which is thin, soft and moisture absorbent such as thin cotton flannel or moisture absorbent synthetic materials that maintain their shape and strength when wet, such materials including non-woven facing materials such as "Pellon". The intermediate layer 42 is a thin, flexible moisture impermeable material such as plastic film or the like.

The stretchable panel 18 is made of a material which is thin, soft and stretchable. Preferably such material should be sufficiently porous to permit the wearer's body to "breathe" to keep the wearer cool. Any number of natural and synthetic fabrics, such as nylon stretch lace can be used. Additionally ventilating eyelets 44 may be provided.

To assemble the panty 10, the layers 40–42 of the panel assembly 16 are laid up with the intermediate layer 42 between the exterior and interior layers 40 and 41 so that the leg cutouts in each coincide. The bottom edge of the central section 30 on the stretchable panel 18 is laid onto the front upper edge 22 of the panel assembly 16 with the forward side edges of the side sections 31 on panel 18 overlapping the front side edges 24 on the panel assembly 16. A seam is then made along the upper front edge 22 of panel assembly 16 and panel 18 and along both of the front side edges 24 to attach the panel 18 to the front section 21 of the panel assembly 16. The thusly connected panel 18 and panel assembly 16 are then folded into the panty shape so that the rear side edges of the side sections 31 of the stretchable panel 18 overlap the back side edges 26 on the panel assembly 16. Seams are then made along these side edges 26 to attach the panel 18 to the back section 19 of the panel assembly 16. The leg openings 15 are finished by installing the bindings 36 around the leg cutouts 28 and the lower edge 32 on the side sections 31. The waist opening 14 is finished by installing the waist binding 34 along the upper edge 35 on panel 18 and the upper edge 25 on the back section 19 of the panel assembly.

Thus, it will be seen that the intermediate moisture impermeable layer 42 separates the interior absorbent layer 41 from the exterior layer 40 to prevent any liquids absorbed by the interior layer 41 from soiling the exterior layer 40. The front section 21 of the panel assembly 16 is sufficiently large to cover the wearer's pubic area while the back section 19 is sufficiently large to cover the wearer's buttock area. Because the moisture impermeable layer 42 is generally non-stretchable yet should be maintained pulled smooth around the wearer, the side sections 31 of the stretchable panel 18 permit the side of the leg openings 15 to adjust to conform to the wearer while maintaining the panel assembly 16 smooth. Further, the central section 30 of the stretchable panel 18 permits the front section 21 of the panel assembly 16 to smoothly conform to the wearer's stomach.

Figure 4:
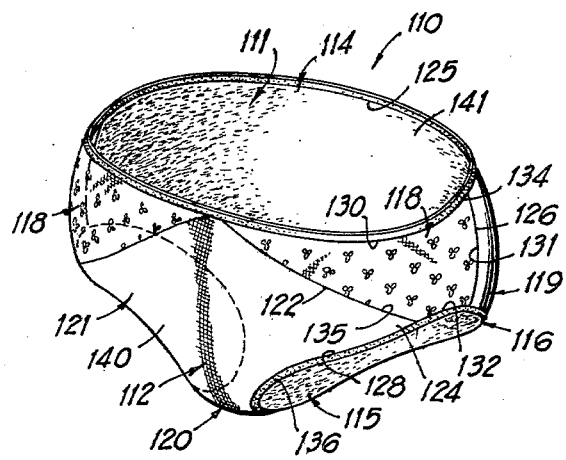
FIG. 4 is a perspective view of a panty construction embodying a second embodiment of my invention.

FIG. 4 of the drawings discloses a second embodiment of the invention incorporated in a panty 110. The reference numbers applied thereto correspond to the reference numbers applied to the panty 10 displaced by 100. Like the panty 10, the panty 110 has an interior 111 and an exterior 112 with a waist opening 114 at its top and pair of leg openings 115 at its lower section so that the panty 110 can be worn similarly to conventional panties. The panty 110 is made up of a non-stretchable panel assembly 116 and a pair of stretch panels 118 so that the panty can conform to different body configurations in the same size range.

The non-stretchable panel assembly 116 has a back section 119, a crotch section 120 and a front section 121. The back section 119 extends from the waist opening 114 down to the crotch section 120, but the front section 121 has an inverted V-shaped top so that the center of the front section 121 extends to the waist opening 114 but the opposite sides thereof terminate at the leg openings 115. Thus, the front section 121 has a pair of downwardly and outwardly angled upper edges 122 which extend from the center of the front section 121 at the waist opening 114 out to the leg cutouts 128. The back section 119 of the non-stretchable panel 116 has an upper edge 125 located along the edge of waist opening 114, and a pair of opposed side edges 126 which extend from opposite ends of the upper edge 125 down to the leg opening 115 and are oriented perpendicular to the edge of the waist opening 114. It will be noted that the front section 121 is sized so that the corners 124 where the upper angled edges 122 meet the leg cutouts 128 are spaced forwardly of the back side edges 126 of the back panel 116 which are spanned by the stretch panels 118.

The stretch panels 118 connect the front section 121 to the back section 122 of the panel assembly 116 to complete the panty shape. Each of the stretch panels 118 has a generally triangular shape with a top edge 130 at about a right angle to the side edge 131. The angled bottom edge 135 extends from the top edge 130 to the leg cutout edge 132 at an angle complementary to the upper angled edges 122 on the front section 121 of the panel assembly 116. Thus, the top edges 130 form continuations of the upper edge 125 on the back section 119 of the panel assembly 116 while the side edges 131 mate with the side edges 126 on the back section 119. The cutout edge 132 forms a continuation of the cutout 128 in the panel assembly 116 to define the leg opening 115.

The waist opening 114 has an elasticized binding 134 sewn along the upper edge 126 of the back section 119 of the panel assembly 116 and the top edges 130 of the stretchable panels 118. Similarly, an elasticized binding 136 is sewn to the panel assembly 116 along each leg cutout 128 and the connecting cutout edge 132 of the stretchable panels 118 to bind each leg opening 115.

Figure 5:
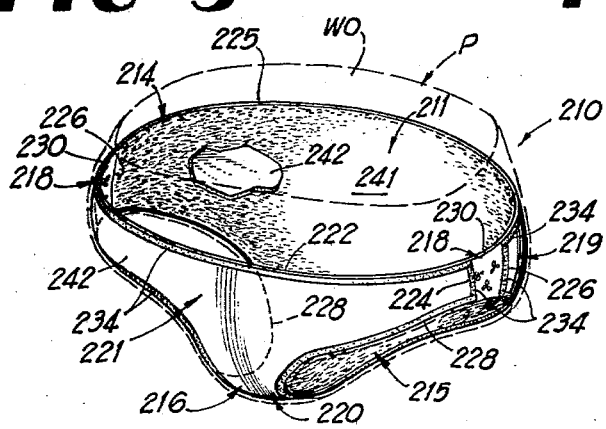
FIG. 5 is a perspective view of a third embodiment of my invention.

The non-stretchable panel assembly 116 has three layers like panel assembly 16, an exterior fabric layer 140, an interior moisture absorbent layer 141, and an intermediate moisture impermeable layer with the three layers in juxtaposition with each other as best seen in FIG. 4. Like the panel assembly 16, all of these layers have the same size and configuration with a front section, a crotch section and a back section along with the leg cutouts so that when they are attached together, the panel assembly 116 is formed. The materials of the layers of the panel assembly 116 and the material of the panels 118 correspond to those of the panty 10. Also, the panty 110 would be assembled similarly to the panty 10. FIG. 5 illustrates a third embodiment of the invention which is adapted to convert a conventional panty P seen by dashed lines. The third embodiment is thus a panty liner 210 having an interior 211 and an exterior 212 with a top opening 214 and pair of leg openings 215 at its lower section so that the panty liner 210 will fit in and can be worn in the conventional panties P. The panty liner 210 is made up of a non-stretchable panel assembly 216 and a pair of stretch panels 218 so that the panty liner can conform to different body configurations in the same size range.

The non-stretchable panel assembly 216 has a back section 219, a crotch section 220 and a front section 221. The back section 219 extends from the top opening 214 down to the crotch section 220, and the front section 221 extends up from the crotch section to the top opening 214. As best seen in FIG. 5, the front section 221 of the non-stretchable panel assembly has an upper edge 222 at the top opening 214 parallel to the edge of the waist opening WO in panties P when liner 210 is in place as seen in FIG. 5. The front section 221 also has a pair of opposed side edges 224 which extend from opposite ends of the upper edge 222 to the leg opening 215 and are oriented generally perpendicular to the edge of the top opening 214. Similarly, the back section 219 of the non-stretchable panel assembly 216 also has an upper edge 225 located along the edge of top opening 214, and a pair of opposed side edges 226 which extend from opposite ends of the upper edge 225 down to the leg opening 215 and are oriented perpendicular to the edge of the top opening 214. It will be noted that the top opening 214 has an edge length which is larger than the sum of the length of the upper edge 225 of the back section 219 plus the length of the upper edge 222 of the front section 221 so that when the panel assembly 216 is formed into the panty shape, the side edges 224 of the front section 221 will be spaced from the side edges 226 of the back section 219. Each stretchable panel 218 connects the side edge 224 on the front section 221 to the side edge 226 on the back section 219 of the panel assembly 216 to complete the panty shape of the liner. The size of the front section 221 and back section 219 of the panel assembly 216 and the stretchable panels 218 are such that when the crotch section 220 of liner 210 is placed in the crotch section of the panty P, the upper edges 224 and 226 on the non-stretchable panel assembly 216 and the top edges 230 on the side stretchable panels 218 lie below the waist opening WO in the panty P as seen in FIG. 5.

The non-stretchable panel assembly 216 has two layers, an interior moisture absorbent layer 241, and an exterior moisture impermeable layer 242 with the layers being in juxtaposition with each other. These layers have the same size and configuration with a front section, a crotch section and a back section along with the leg cutouts so that when they are attached together, the panel assembly 216 is formed. The interior layer 241 corresponds to the layer 41 in the first embodiment of the invention while the exterior layer 242 corresponds to the intermediate layer 42 in the first embodiment of the invention.

To hold the liner 210 in place in the panty P, an adhesive strip 234 may be provided on the outside of the panel assembly 216 adjacent the upper edges 222 and 226, the side edges 224 and 225 and the leg cutouts 228. When the liner 210 is installed, the fabric of the panty P is stretched smooth over the panel assembly 216 and the adhesive strips 234 stuck to this fabric. The side stretchable panels 218 do not have adhesive applied thereto and thus permit the liner 210 to conform to the wearer's body to keep the panel assembly 216 smooth.

FIGS. 6-8 illustrate a fourth embodiment of the invention which is also adapted to convert a conventional panty P. The fourth embodiment is thus a panty liner 310 having an interior 311 and an exterior 312 so that the panty liner 310 will fit in and can be worn in the conventional panties P. The panty liner 310 includes a non-stretchable panel assembly 316 which is removably attachable to the panty P so that both the panty P and the panty liner 310 can conform to different body configurations in the same size range.

The non-stretchable panel assembly 316 has a back section 319, a crotch section 320 and a front section 321. The back section 319 is sized to extend from the waist opening WO in the panty P down to the crotch section 320 in juxtaposition with the crotch section of the panty P, and the front section 321 extends up from the crotch section 320 to a point below the waist opening WO in panty P.

As best seen in FIG. 6, the front section 321 of the non-stretchable panel assembly has an upper edge 322 at its top spaced below and parallel to the edge of the waist opening WO in panties P when liner 310 is in place as seen in FIG. 7. The front section 321 also has a pair of opposed side edges 324 which extend from opposite ends of the upper edge 322 to the leg cutouts 328 and are oriented generally perpendicular to the upper edge 322. Similarly, the back section 319 of the non-stretchable panel assembly 316 also has an upper edge 325 located along the edge of the waist opening WO, and a pair of opposed side edges 326 which extend from opposite ends of the upper edge 325 down to the leg cutouts 328 and are oriented perpendicular to the upper edge 325. It will be noted that the waist opening WO in panty P has an edge length which is larger than the sum of the length of the upper edge 325 of the back section 319 plus the length of the upper edge 322 of the front section 321 so that when the panel assembly 316 is formed into the panty shape, the side edges 324 of the front section 321 will be spaced from the side edges 326 of the back section 319.

The non-stretchable panel assembly 316 has two layers, an interior moisture absorbent layer 341, and an exterior moisture impermeable layer 342 with the layers being in juxtaposition with each other. These layers have the same size and configuration with a front section, a crotch section and a back section along with the leg cutouts so that when they are attached together, the panel assembly 316 is formed. The interior layer 341 corresponds to the layer 41 in the first embodiment of the invention while the exterior layer 342 corresponds to the intermediate layer 42 in the first embodiment of the invention.

To hold the liner 310 in place in the panty P, adhesive strips 334 are provided on the outside of the panel assembly 316 adjacent the upper edges 322 and 326, the side edges 324 and 325 and the leg cutouts 328. When the liner 310 is installed, the fabric of the panty P is stretched smooth over the panel assembly 316 and the adhesive strips 234 stuck to this fabric. The liner 310 relies on the material of the panty P to keep it located, yet because the side edges 324 and 325 do not overlap and are not attached to each other, both the panty P and the liner 310 can conform to the wearer's body to keep the panel assembly 316 smooth.

FIG. 9 illustrates a fifth embodiment of the invention which is a modification of the fourth embodiment of the invention. For sake of simplicity, reference numbers corresponding to those applied to the fourth embodiment displaced by 100 are applied to the fifth embodiment. Only the differences will be described in detail. It will be seen that the fifth embodiment is a panty liner 410 adapted to be used similarly to the panty liner 310.

The non-stretchable panel assembly 416 has a front section 421, crotch section 420 and back section 419 sized similarly to that of panty liner 310. Thus, front section 421 has an upper edge 422 and side edges 424 while back section 419 has an upper edge 425 and side edges 426. Unlike the fourth embodiment, the panel assembly 416 has three layers, an interior layer 441, an exterior layer 442, and an intermediate layer 445. The intermediate layer 445 is sandwiched between the interior and exterior layers 441 and 442. The exterior layer 442 corresponds to the exterior layer 342 of the panty liner 310 and is thus moisture impermeable. The interior layer 441 is moisture permeable and may be absorbent. Layer 441 should be soft because of its contact with the wearer's skin and may be made of a variety of materials both woven and non-woven. The material of layer 441 must maintain its strength when wet as is apparent. The intermediate layer 445 is highly moisture absorbent so that liquid penetrating the interior layer 441 will be absorbed thereby. It is not necessary that the intermediate layer 445 have good wet strength characteristics since it is supported between layers 441 and 442. Any number of materials may be used for layer 445 such as a fibrous cellulosic material as long as the material is highly absorbent.

The adhesive strips 434 hold the panty liner 410 in place similarly to the liner 310. This allows the liner 410 and the panty in which it is installed to adjust to the wearer's body configuration.

I claim:

1. A panty construction having a waist opening at its top and a pair of leg openings at its bottom comprising:
   a non-stretchable panel assembly including a front section, a back section and a crotch section joining the front and back sections; said panel assembly formed into a panty shape and defining a pair of leg cutouts therein forming a portion of the leg openings in the panty construction, said front section defining opposed front side edges and a front upper edge thereon, said front side edges extending upwardly from the top of the leg openings toward the waist opening and said front upper edge extending between said front side edges, said front upper edge spaced below and generally parallel to the waist opening, said back section defining opposed rear side edges thereon extending upwardly from the top of the leg openings toward the waist opening, said rear side edges spaced from said front side edges at the top of the leg openings; said panel assembly including:
   an exterior fabric layer;
   an interior liquid absorbent layer; and
   an intermediate liquid impermeable layer between and separating said exterior fabric layer from said interior absorbent layer to prevent liquids absorbed by said interior absorbent layer from penetrating said exterior fabric layer; and
   a stretchable panel connecting the front and back sections of said non-stretchable panel assembly to complete the panty shape, said stretchable panel including a central section connected to said front upper edge of said front section and extending to said waist opening and a pair of side sections integral with opposite ends of said central section, each of said side sections extending between said front and rear side edges on said front and rear sections of said non-stretchable panel assembly from the top of the leg opening to the waist opening, each of said side sections connected to said front and rear side edges on said front and rear sections of said non-stretchable panel assembly so that said side sections of said stretchable panel permits relative movement between said front and back side edges of said front and back sections of said non-stretchable panel assembly over the leg openings to allow the panty construction to conform to different wearer body configurations in the same size range and said central section permits relative movement of said front upper edge on said front section of said non-stretchable panel assembly with respect to the waist opening to permit the panty construction to adjust to different abdomen configurations in the same size range.

2. The panty construction of claim 1 wherein the back section of said panel assembly extends to the waist opening in the panty construction and defines a back upper edge thereon extending along the waist opening.

3. The panty construction of claim 2 wherein said stretchable panel is air permeable to permit ventilation.

4. The panty construction of claim 3 further including an elastic binding extending around the waist opening and connected to said stretchable panel and the back upper edge on said back section of said non-stretchable panel.

5. The panty construction of claim 4 further including a pair of elastic leg bindings, one of said leg bindings extending around each of the leg openings and connected to said non-stretchable and stretchable panels around the leg opening.

* * * * *